United States Patent
Carnevale

(10) Patent No.: US 7,830,424 B2
(45) Date of Patent: Nov. 9, 2010

(54) HAZE REDUCTION METHOD AND APPARATUS FOR USE IN RETINAL IMAGING

(76) Inventor: Matthew Carnevale, 26 Foss St., Medford, MA (US) 02155

( * ) Notice: Subject to any disclaimer, the term of this patent is extended or adjusted under 35 U.S.C. 154(b) by 1093 days.

(21) Appl. No.: 11/240,607

(22) Filed: Sep. 30, 2005

(65) Prior Publication Data

US 2007/0076111 A1    Apr. 5, 2007

(51) Int. Cl.
*H04N 5/217*    (2006.01)
*H04N 9/64*    (2006.01)
*H04N 5/225*    (2006.01)

(52) U.S. Cl. ..................... 348/241; 348/244; 348/207.1

(58) Field of Classification Search .................. 348/61, 348/77, 78, 192, 207.99, 207.1, 241, 243, 348/244, 250, 251, 317, 365, 367, 373, 374, 348/375, 211.14
See application file for complete search history.

(56) References Cited

U.S. PATENT DOCUMENTS

| | | | | |
|---|---|---|---|---|
| 5,859,669 A | * | 1/1999 | Prentice ....................... | 348/469 |
| 5,987,543 A | * | 11/1999 | Smith ........................... | 710/70 |
| 6,480,180 B1 | * | 11/2002 | Moon ........................... | 345/98 |
| 6,515,271 B1 | * | 2/2003 | Shimizu .................. | 250/208.1 |
| 6,583,659 B1 | * | 6/2003 | Kwong et al. ............... | 327/295 |
| 6,836,290 B1 | * | 12/2004 | Chung et al. ................. | 348/294 |
| 7,050,032 B2 | * | 5/2006 | Tamura ....................... | 345/98 |
| 7,283,132 B2 | * | 10/2007 | Ishibashi et al. ............ | 345/212 |
| 2007/0076111 A1 | * | 4/2007 | Carnevale ................... | 348/311 |

* cited by examiner

*Primary Examiner*—David L Ometz
*Assistant Examiner*—Peter Chon
(74) *Attorney, Agent, or Firm*—Robert K. Tendler

(57) ABSTRACT

Driver current in digital retinal image transfer is significantly reduced for retinal cameras for reducing heat-induced dark current and resultant haze. In one embodiment line drivers are used whose current draw does not depend on data rate or frequency to eliminate the problem of high data rates creating high driver current draw. In a second embodiment the 14-MHz clock driver is inhibited by interrupting its free-running clock pulse input until such time as one wishes to output a picture from the retinal camera, at which time the clock driver draws only a quick burst of current. The result is much lower overall clock driver current draw, less heat, less dark current and less haze.

17 Claims, 4 Drawing Sheets

HAZE REDUCTION METHOD AND APPARATUS FOR USE IN RETINAL IMAGING

FIELD OF THE INVENTION

This invention relates to retinal imaging and more particularly to a method and apparatus for reducing haze.

BACKGROUND OF THE INVENTION

Retinal cameras that transfer digital camera images using digital transmission between the camera and the image-rendering system have been employed in the past to take the 6- to 11-megapixel digital camera outputs and transfer the data over parallel lines in a cable to follow-on processing. Thus, the images from retinal cameras are transmitted to either a local processor over for instance 10 feet, or around the world so that the digital images may be remotely displayed.

There has however been a problem with haze due to the dark currents induced by circuits housed within the camera. The current draw of these circuits causes the CCD sensor array to heat up in a matter of minutes. This results in images containing haze because the sensor array in the camera has difficulty distinguishing between heat and light. It will be appreciated that haze obscures the detail in the retinal image because it ruins contrast. Instead of images appearing black, nothing in the image looks black but rather gray. Thus the thermally induced haze deadens contrast.

It will be appreciated that retinal cameras have utilized analog systems for transferring the data from the digital camera array to a remote location.

However, if the information is transferred in analog form, the transmission is oftentimes corrupted by outside noise. It will be appreciated that the CCD sensor pixels have output voltages proportional to the incident light. Thus, for each pixel, one obtains a voltage change that can be measured. In the analog domain, one takes the voltage information and amplifies it before coupling it by a cable to a computer. It is noted that these analog voltages are directly transmitted and are not analog-to-digital converted into digital equivalents at the camera.

The problems with such analog systems are that, as the signals go down the cable, they are susceptible to noise, whether it be magnetic, electromagnetic, fluorescent light noise or even power line noise. Oftentimes the analog signals can be corrupted by cross talk in which the lines in the cable are wrapped around the same bundle that is generating the noise. By amplifying the signals in these cables to permit long distance signaling the noise is amplified.

Such an analog system is manufactured by Megavision and although the camera itself is in a smaller package than those employing digital data transfer, the digital transfer of image information along a cable is much less susceptible to the aforementioned noise sources.

In order to get away from the analog transmission of data, digital cameras today convert the sensor outputs within the camera to, in one embodiment, 12 bits of data that is transmitted in parallel using differential line drivers and twisted pairs so that for 12 bits of information, one drives 24 wires.

By operating in the digital domain one achieves clean signals that can be sent thousands of feet without corruption.

While digital data transfer is preferable from the noise corruption point of view, it is much more complicated than analog systems. This is because more circuitry is required, which draws more power. Thus the circuits utilized in the analog-to-digital conversion and the line driving consume a fair amount of power that generates heat within the camera. Moreover, when utilizing digital communications streams, the communication protocols are much more complicated in the analog protocols. If one wants to send an analog voltage to a remote location, all one needs is a ground and the voltage. However, in sending digital data, for instance in a 12-bit system, there must be at least 12 lines. Note in 12-bit transfer the sensor pixel value can be anywhere from 0 to 4,095.

The digital information is clocked down the cable, in one embodiment at 14 MHz, which is the clock frequency normally employed. Thus the data rate or frequency associated with such retinal image data transmission systems is relatively high.

It might be thought that one could use serial data and transmit the serialized data down a coaxial cable. However, serial connections are relatively slow, especially when considering that one picture contains as many as 6 to 11 megapixels that must be transmitted down the line every second. Thus even with serial methods such as firewire, the amount of data transmitted is limited. When utilizing a parallel system in which each of the 12 bits is dedicated to a wire pair, the transmission is much faster due to the parallel interface.

Note, in a 12-bit system the differential line drivers employed in the camera drive 24 lines, with at least four other hand-shaking signals adding another 8 lines.

While the cause of dark current was assumed to be the current draw of the circuits used within the digital camera, it was not immediately clear what the source of this current was. Analysis has shown that he majority of the current draw is from the line drivers and the clock driver. Thus while dark current is not much of an issue with analog cameras, the heat associated with the current draw in digital transmission systems changes the properties of the CCD sensor in a matter of minutes.

After analysis of the power consumption of the retinal camera circuits, it was found that the drivers were pulling as much as 2 amps, which significantly degrades the retinal camera images such that after a minute or two one is seeing haze. As mentioned hereinbefore, if the image is hazy, detail is obscured because of the lack of contrast between the dark areas and the light areas in the image. As will be appreciated, when looking at an image corrupted by haze, nothing black appears black but rather gray.

SUMMARY OF INVENTION

Part of the subject invention is the recognition that the majority of the dark current in the retinal camera comes from the line drivers and the clock driver. It was not immediately obvious which circuits within the digital camera were creating significant haze, but after isolation and testing it was found that the line drivers and clock driver were pulling a significant amount of current. Noting that a 12-bit system requires the driving of 24 lines, it became clear that the number of lines supported by the line drivers dictated the total current draw.

The problem was how to be able to reduce the current draw for the line drivers.

It was found that most of the line drivers had a current draw that was proportional to the frequency or data rate at which the driver was operated. This discovery indicated that perhaps the current drawn by the line drivers could be reduced if the frequency or data rate could be reduced.

After some trial and error, it was determined that in order for real-time image transfer, the 14-MHz clock rate was indeed important and while the frequency of the signals through the line drivers did vary, the data rate was nonetheless dictated by the clock rate. Thus it became impractical to solve the current draw problem by reducing the data rate or frequency.

In trying to determine the availability of lower power consumption drivers, it was found that one class of drivers were not frequency-dependent in terms of power consumption.

For a 12-bit system it was found that one could reduce the current draw from 1.0 amps to approximately 0.6 amps by using frequency-independent ultra low-power line drivers as opposed to the standard drivers. The use of these frequency-independent drivers resulted in a significant reduction in the overall power consumption of the drivers and significantly reduced or eliminated haze in the retinal images.

Thus retinal images could be captured and transmitted without regard to the length of time that the sensor array was subjected to dark current heating. The result is that one could use digital signaling to eliminate noise problems while at the same time preventing haze buildup due to dark currents.

While for a 12-bit system one required the driving of 24lines, there was still a circuit element that was consuming a considerable amount of power and that was the ubiquitous clock driver. Again it was determined that reducing the clock rate would significantly impair real-time rendering of retinal images. As a result, the problem of haze production due to the high clocking rate persisted.

As part of the subject invention, it was found that while one could not reduce the clocking rate to achieve lower power drain, it was possible to gate the clock driver on only at the time when one was transferring digital image data. Thus the time interval in which the clock driver is drawing current is one-to-one associated with transmitting a frame of the image in parallel over the digital link.

Because the clock driver was only turned on during image transfer, it was found that it was possible to reduce the overall average current draw from 0.6 amps to 0.2 amps, thus all but eliminating haze.

Instead of continuously driving a clock driver with free running clock pulses, in one embodiment the free-running clock to the driver is gated so that clock pulses are coupled to the input to the clock driver only when there is an active transmission on the line. With no input, the clock driver has no signal to amplify and thus draws only a minute amount of current. One thus provides an amplified clock pulse output only for a short period of time during transmission of a frame, thus reducing overall clock driver current draw.

Since there are framing signals generated within the camera relating to when a frame is active, one can piggyback the gating of the clock pulses from the free-running clock to the clock driver.

The result of using frequency-independent line drivers and interrupting the pulses to the clock driver is that one can reduce the overall average current draw by five times from, for instance, 0.1 amps to 0.2 amps and thereby significantly eliminate haze.

The result is that one can have a haze-free image similar to that achieved with analog systems but with no external noise corruption.

In summary, driver current in digital retinal image transfer is significantly reduced for retinal cameras for reducing heat-induced dark current and resultant haze. In one embodiment line drivers are used whose current draw does not depend on data rate or frequency to eliminate the problem of high data rates creating high driver current draw. In a second embodiment the 14-MHz clock driver is inhibited by interrupting its free-running clock pulse input until such time as one wishes to output a picture from the retinal camera, at which time the clock driver draws only a quick burst of current. The result is much lower overall clock driver current draw, less heat, less dark current and less haze.

BRIEF DESCRIPTION OF THE DRAWINGS

These and other features of the subject invention will be better understood in connection with a Detailed Description, in conjunction with the Drawings, of which.

DETAILED DESCRIPTION

Figure 1:
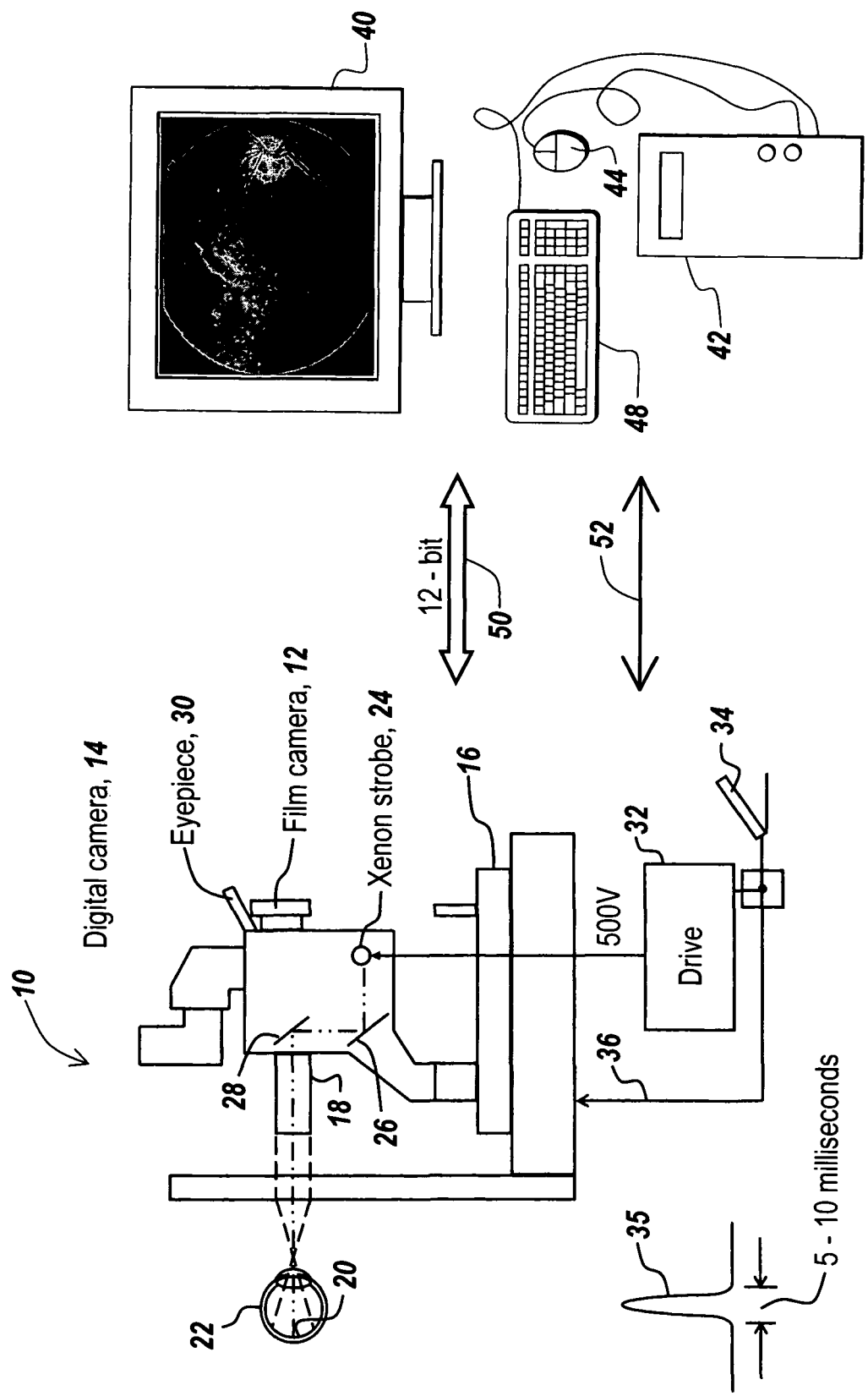
FIG. 1 is a diagrammatic illustration of a retinal camera in which signals from the sensor array of the camera are analog-to-digital converted into a 12-bit stream that is transmitted for further computer processing and image formation.

Referring now to FIG. 1, by way of background a retinal imaging camera 10 includes a film camera 12 and a digital camera 14 mounted on a stand 16 such that an imaging system 18 images the retina 20 of eye 22 onto the focal planes of cameras 12 and 14. In order to illuminate retina 20, a xenon strobe lamp 24 has its output redirected by mirrors 26 and 28 out through imaging system 18 so that the output of xenon strobe 24 illuminates retina 20. Note that an eyepiece 30 is used for focusing both the digital and film camera as well as directing the optics to the appropriate portion of the eye. In one embodiment the strobe is flashed based on toggling of a foot switch 34.

It will be appreciated that foot switch 34 is also used to control camera 10 over line 36 to take the pictures such that any shuttering and exposure for either the film camera or the digital camera is controlled responsive to foot switch 34; or is actuated automatically if desired.

Note in this figure, a monitor 40 is used to display the image from digital camera 10 in FIG. 1, with the xenon flash drive 32 controlled by a computer 42 to set the output of the xenon strobe. Computer 42 inputs include a mouse 44 and a keyboard 46.

Data transfer from camera to computer is provided over a 12-bit data transfer link indicated by arrow 50. In one embodiment the analog image from the digital camera is analog-to-digital converted into a 12-bit stream that is transmitted over a multi-wire twisted pair cable to the downstream processing associated with computer 42.

With analog transmission of retinal images, the distance illustrated by arrow 52 between the digital camera and the downstream processing is critical. As mentioned hereinbefore, the analog signals can be readily corrupted by electromagnetic interference, magnetic interference, and by AC line noise and the like, which makes an analog transmission system undesirable. However, by using a digital transmission mode in which data in one embodiment is transmitted in parallel to computer 42, the distance between the camera and the follow-on processing is only dependent on the amplification provided by the line drivers.

As mentioned above, the digital transmission mode requires analog-to-digital converters at the camera and the use of differential line drivers as well as drivers for control signals, including the clock signal that is used in the data transfer operation.

Figure 2:
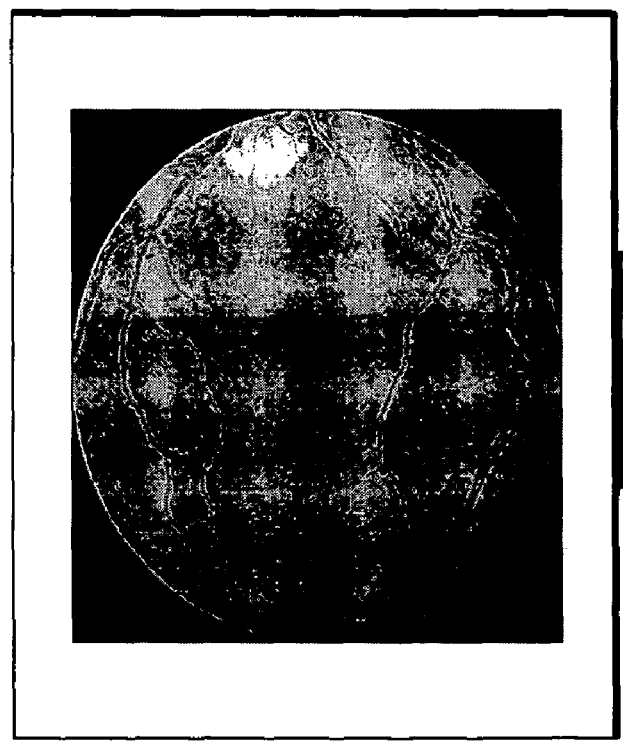
FIG. 2 is a photograph of a retinal image of one eye of a patient in which haze obscures retinal features.

Referring to FIG. 2, what can be seen is the retinal image of one eye of a patient that has been corrupted with haze such that what detail that exists in the photograph is obscured due to the graying out of the image. This contrast reduction due to haze in some cases prevents diagnosis because it can obscure some of the detail that could make diagnosis possible. The haze is due to dark current production from the digital camera circuitry that heats up the sensor array used in the camera. Since the sensor array cannot distinguish readily between heat and light, it interprets all incident radiation as coming from the image and produces an output responsive not only to the light image but also to heat.

Figure 3:
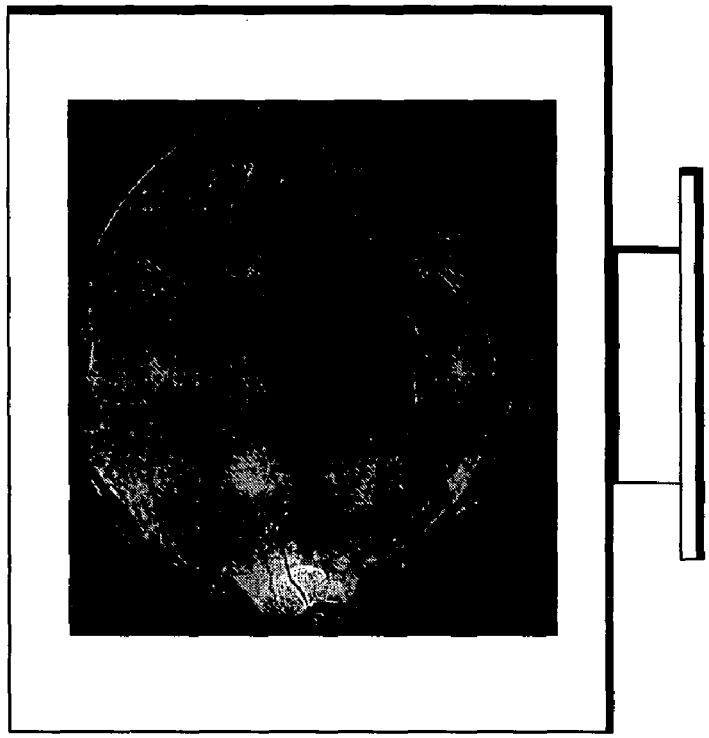
FIG. 3 is a photograph of a retinal image of the other eye of the patient in FIG. 2 in which the retina of the other eye is rendered without haze.

Referring to FIG. 3, it can be seen from the photograph that retinal image detail of the other eye of the patient referred to in FIG. 2 is restored through the use of the subject system so that, with the techniques described hereinafter, one can provide a retinal image uncorrupted by haze.

Figure 4:
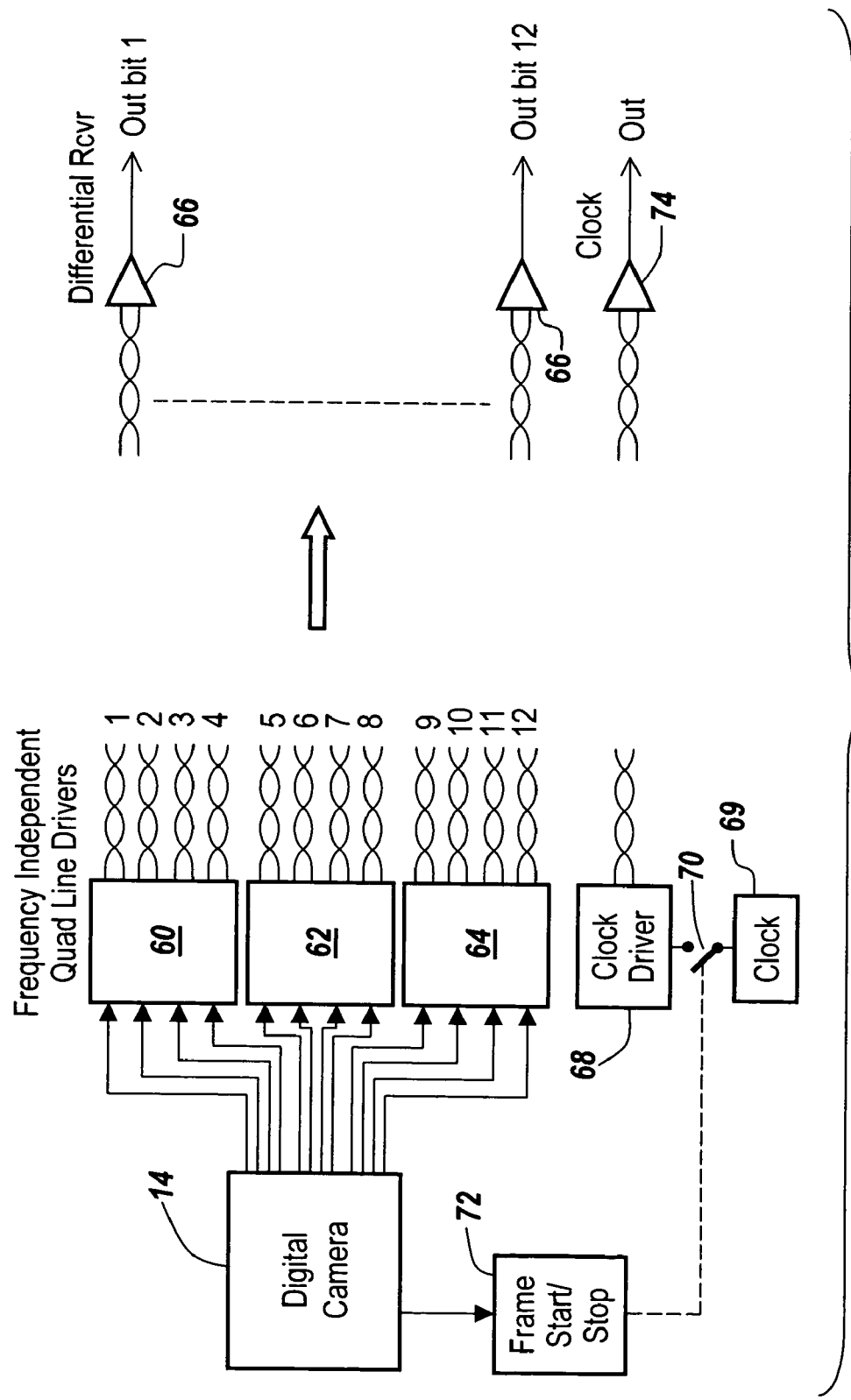
FIG. 4 is a diagrammatic illustration of a digital camera outputting 12 bits of data to three differential frequency-independent quad drivers that in turn drive twisted pairs, also showing the interruption of the clock pulses to the clock driver based on a frame of transmitted data; and, FIG. 5 is a schematic diagram showing the use of differential line drivers and a clock driver for the generation of differential signals applied to twisted pairs.

Referring now to FIG. 4, digital camera 14 has within it a number of frequency-independent differential quad line drivers 60, 62 and 64 that take the analog-to-digital converted signals from camera 14, amplify them and couple the amplified signals to twisted pairs, here illustrated by numerals 1-12. This corresponds to the parallel transmission of data over 24 twisted pairs to computer 42, which inter alia has receivers 66 used to detect binary coded signals transmitted.

The differential quad line drivers are those that have power consumption that is independent of frequency or baud rate. Each of the differential drivers has a differential positive and a negative output that drives the associated twisted pair, with the twisted pair being used to cancel any environment-induced noise.

In one embodiment the frequency-independent differential quad line drivers are available from National Semiconductor as Model DS90C031™, which are described as high data rate drivers having ultra-low power dissipation using low-voltage differential signaling. The driver is a current-mode driver having a balanced current source design that makes the driver current draw frequency-independent. A current mode driver has a high output impedance and supplies a constant current for a range of loads. This driver is also referred to as using Low Voltage Differential Signaling (LVDS) technology.

With respect to the clock driver, here illustrated at 68, as part of the subject invention the clock driver is driven with clock pulses only when there is an active data transmission over the line. In one embodiment the clock driver is a differential driver that amplifies the pulses from a free-running clock and only draws power when clock pulses are applied to its input. To this end, a free-running clock 69 is coupled to a switch 70 controlled by an elongated framing pulse from the camera sensed by detector 72. When the detected framing pulse is high indicating an active transmission, switch 70 gates the clock pulses to the clock driver that drives a twisted pair line. This twisted pair line is in turn coupled to a receiver 74.

Thus clock pulses are coupled to the clock driver only during the transmission of a frame of image information. The result is that even when operating in the voltage mode, the average current draw is minimized when using this intermittent clock driver. The net sum is that with such an intermittent clock driver, one minimizes heat and haze such that, as mentioned hereinbefore, the overall current consumption for the drive circuitry is reduced.

Figure 5:
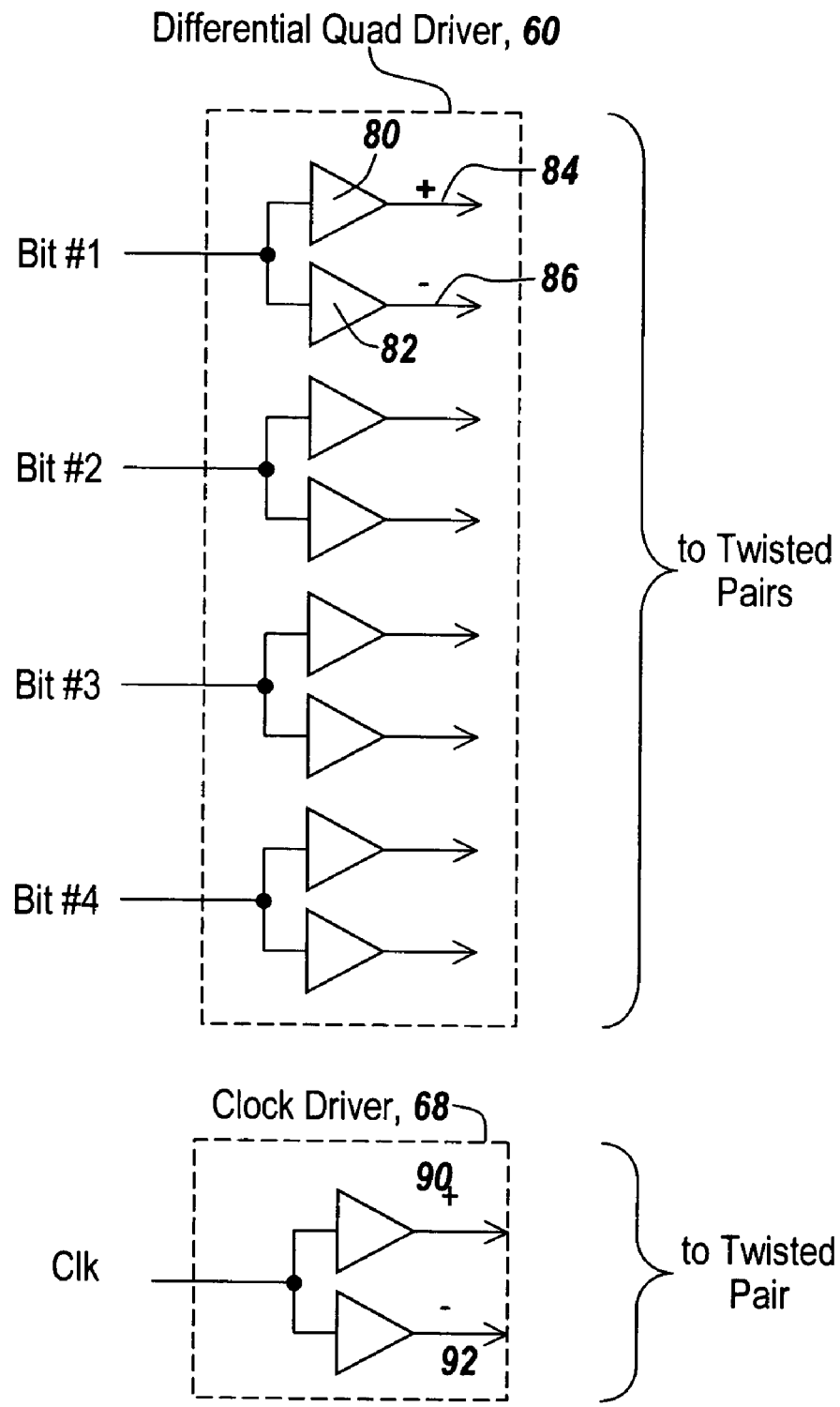

Referring to FIG. 5, each of the differential line drivers in quad driver 60 includes dual amplifiers 80 and 82 that produce differential positive- and negative-going signals at outputs 84 and 86 so that, for instance, bit 1 is converted into two oppositely polarized voltages available on the output lines coupled to the associated twisted pair. Likewise, clock driver 68 includes dual amplifiers 90 and 92 to output differential oppositely polarized voltages to the associated twisted pair.

What will be seen is that through the use of drivers whose ultra-low current draw is frequency-independent and by interrupting the clock driver and gating it on only when required to transmit active data, the overall average current consumption of the circuits that are used to transmit the digital data stream from the retinal camera to follow-on processing can be minimized to the point of dramatically reducing or completely eliminating haze in the retinal images.

While the present invention has been described in connection with the preferred embodiments of the various figures, it is to be understood that other similar embodiments may be used or modifications or additions may be made to the described embodiment for performing the same function of the present invention without deviating therefrom. Therefore, the present invention should not be limited to any single embodiment, but rather construed in breadth and scope in accordance with the recitation of the appended claims.

What is claimed is:

1. A method for reducing haze associated with the heating of sensor array elements in a digital CCD retinal camera coupled over a cable to a follow-on processor, comprising the steps of:
    providing a high resolution digital CCD retinal camera with line drivers whose current draw is both frequency-independent and minimalized; and
    providing a clock driver on a transmitting side driven by clock pulses from a free running clock coupled to an input of the clock driver, the clock driver being different from line drivers, the driving clock pulses input to the clock driver from the free running clock being inhibited by gating such that the coupling of the driving clock pulses to the input of the clock driver is inhibited until such time as the retinal camera outputs a retinal image, such that haze that is the result of dark current is limited by the frequency-independent low current draw of the line drivers and an intermittent current draw of the clock driver due to the gating of the driving clock pulse input thereto.

2. The method of claim 1, wherein the sum of the current draw of both line drivers and the clock driver is less than 0.2 amps, whereby sensor heating and consequent image haze is minimized.

3. The method of claim 1, wherein the line drivers transmit 12 bits of data and include 12 differential line drivers for driving 24 twisted pair lines.

4. A system for transmitting retinal images from a digital retinal camera to a remote location over a transmission line, comprising:
    a CCD retinal camera having a digitally-encoded output;
    a plurality of differential line drivers coupled to said digital output, said line drivers characterized by a low current draw in which the low current draw is frequency independent;
    a number of twisted pairs coupled to associated outputs of said differential line drivers for transmitting the digitally-encoded image to said remote location;

a clock driver on a transmitting side driven by clock pulses input thereto from a free running clock, the clock driver being different from said line drivers; and, a gating circuit for gating said clock pulses from an input of the clock driver such that a coupling of the clock pulses to the input of the clock driver is inhibited until a digital image is to be transmitted to said remote location, whereby the amount of current drawn by said line drivers is minimized and is not dependent on frequency, and wherein the average current draw by said clock driver is minimized due to its intermittent use, whereby heat buildup in said retinal camera is minimized to minimize haze in the image rendered at said remote location.

5. The system of claim 4, wherein said clock rate is in the 14-MHz range and wherein the total current draw of said divers is less than 0.2 amps.

6. The system of claim 4, wherein said digital camera includes a 12-bit digital output and wherein said line drivers include three frequency-independent differential quad drivers.

7. The system of claim 4, wherein said differential line drivers include low-voltage differential signaling technology.

8. The system of claim 4, wherein said line drivers include current mode drivers having a high output impedance and include constant current sources for a range of loads.

9. The system of claim 8, wherein said line drivers are ultra-low power dissipation line drivers.

10. The system of claim 4, wherein said frequency-independent line drivers include current mode line drivers having constant current sources for a range of loads to provide said frequency-independent current draw operation.

11. The system of claim 4, wherein said clock driver includes a free-running clock and wherein said gate includes a switch for connecting said free-running clock to said clock driver in accordance with framing signals within said digital camera.

12. A method of reducing haze in a high resolution CCD retinal camera, comprising the steps of:

minimizing heat associated with the current draw associated with line drivers and a transmitting side clock driver used to generate signals applied to a receiving side clock, the line drivers and the clock drivers used in transmitting images from the retinal camera to a remote location over twisted pairs by using an ultra low current draw differential line driver, the current draw of the line driver being independent of frequency, and by intermittently driving the transmitting side clock driver separate from the line drivers, the clock driver being driven by clock pulses input thereto from a free running clock with the driving clock signals being gated from an input of the clock driver such that a coupling of the driving clock pulses to the input of the clock driver is inhibited until an image is to be transmitted to the remote location, such that driver current drawn is reduced to a point at which heating of the digital CCD camera is minimized to such an extent that heat-induced haze is virtually eliminated.

13. The method of claim 12, wherein the line drivers are current drivers and have current sources that supply a constant current for a range of loads, thereby to make the line driver current draw frequency-independent.

14. The method of claim 13, wherein the images transmitted to the remote location are transmitted at a clock frequency in the 14-MHz range, thus to provide rendering of real-time retinal images without haze at the remote location.

15. The method of claim 14, wherein the line drivers employ low-voltage signaling technology.

16. The method of claim 12, wherein the digital camera employs framing signals and wherein the intermittent clock driver is gated on and off in accordance with the framing signals.

17. The method of claim 16, wherein the step of gating the clock driver includes the steps of providing a continuous source of clock pulses and coupling the continuous source of clock pulses to the clock driver only when there is an active transmission.

* * * * *